US012193683B2

(12) United States Patent
Kuyler et al.

(10) Patent No.: US 12,193,683 B2
(45) Date of Patent: Jan. 14, 2025

(54) CUT GUIDE WITH INTEGRATED JOINT REALIGNMENT FEATURES

(71) Applicant: Treace Medical Concepts, Inc., Ponte Vedra, FL (US)

(72) Inventors: Adriaan Kuyler, Ponte Vedra, FL (US); Jody McAleer, Jefferson City, MO (US); William DeCarbo, Pittsburgh, PA (US); Robert Santrock, Morgantown, WV (US); Sean Scanlan, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 412 days.

(21) Appl. No.: 17/750,275

(22) Filed: May 20, 2022

(65) Prior Publication Data

US 2022/0370082 A1 Nov. 24, 2022

Related U.S. Application Data

(60) Provisional application No. 63/246,792, filed on Sep. 21, 2021, provisional application No. 63/190,787, filed on May 20, 2021.

(51) Int. Cl.
*A61B 17/15* (2006.01)
*A61B 17/16* (2006.01)
(Continued)

(52) U.S. Cl.
CPC ........ *A61B 17/151* (2013.01); *A61B 17/1682* (2013.01); *A61B 17/1775* (2016.11); *A61B 17/66* (2013.01); *A61B 2017/565* (2013.01)

(58) Field of Classification Search
CPC ....... A61B 17/56; A61B 17/02; A61B 17/025; A61B 17/15; A61B 17/151; A61B 17/88;
(Continued)

(56) References Cited

U.S. PATENT DOCUMENTS 3,664,022 A  5/1972 Small
4,069,824 A  1/1978 Weinstock
(Continued)

FOREIGN PATENT DOCUMENTS

AU  2009227957 B2  7/2014
CA  2491824 A1  9/2005
(Continued)

OTHER PUBLICATIONS

"Accu-Cut Osteotomy Guide System," BioPro, Brochure, Oct. 2018, 2 pages.
(Continued)

*Primary Examiner* — Christopher J Beccia
(74) *Attorney, Agent, or Firm* — Fredrikson & Byron, P.A.

(57) ABSTRACT

A bone cutting and joint realignment instrument may include an integrated spacer body, bone preparation guide, and fulcrum body. The spacer body is configured to be inserted into a joint space between a metatarsal and an opposed cuneiform of a foot. The bone preparation guide body is affixed to the spacer body with the spacer body extending downwardly from the bone preparation guide body. The bone preparation guide body can define at least one guide surface configured to be positioned over at least one of the metatarsal and the opposed cuneiform. The fulcrum body may be rotatably coupled to the spacer body within a bounded range of rotation, such as a bounded range of less than 45 degree. The fulcrum body can be configured to be inserted in an intermetatarsal space between the metatarsal and an adjacent metatarsal.

37 Claims, 11 Drawing Sheets

(51) Int. Cl.
 *A61B 17/17* (2006.01)
 *A61B 17/66* (2006.01)
 *A61B 17/56* (2006.01)

(58) Field of Classification Search
 CPC .. A61B 17/8866; A61B 17/17; A61B 17/1775
 See application file for complete search history.

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Puddu |
| 5,779,709 A | 7/1998 | Harris, Jr. et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | Mcguire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | Von Hoffmann et al. |
| 6,547,793 B1 | 4/2003 | Mcguire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | Mcguire |
| 7,033,361 B2 | 4/2006 | Collazo |
| 7,097,647 B2 | 8/2006 | Segler |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plaky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |

(56) References Cited

U.S. PATENT DOCUMENTS

| | | |
|---|---|---|
| 8,496,662 B2 | 7/2013 | Novak et al. |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Play et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Wright et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| 9,113,958 B2 | 8/2015 | Coceancig |
| D740,424 S | 10/2015 | Dacosta et al. |
| D765,844 S | 9/2016 | Dacosta |
| D766,434 S | 9/2016 | Dacosta |
| D766,437 S | 9/2016 | Dacosta |
| D766,438 S | 9/2016 | Dacosta |
| D766,439 S | 9/2016 | Dacosta |
| 9,452,057 B2 | 9/2016 | Dacosta et al. |
| 9,522,023 B2 | 11/2016 | Haddad et al. |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,779,867 B2 | 9/2020 | Penzimer et al. |
| 11,304,705 B2 | 4/2022 | Fallin et al. |
| 11,571,312 B1 | 2/2023 | Parekh et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | Mcnamara |
| 2006/0129163 A1 | 6/2006 | Mcguire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |

(56) References Cited

U.S. PATENT DOCUMENTS

| | | |
|---|---|---|
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Wright et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Anderson et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0042598 A1 | 2/2017 | Santrock et al. |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0344334 A1 | 12/2018 | Kim et al. |
| 2020/0015865 A1 | 1/2020 | Lamm et al. |
| 2020/0375645 A1 | 12/2020 | Santrock et al. |
| 2021/0038212 A1 | 2/2021 | May et al. |
| 2021/0077192 A1 | 3/2021 | Perler et al. |
| 2022/0409222 A1 | 12/2022 | Cundiff et al. |
| 2023/0255651 A1 | 8/2023 | Cundiff et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 231718 A | 4/1925 |
| GB | 2154143 A | 9/1985 |
| GB | 2154144 A | 9/1985 |
| GB | 2334214 B | 1/2003 |
| JP | 63005739 A | 1/1988 |
| JP | 05031116 A | 2/1993 |
| JP | 2004174265 A | 6/2004 |
| JP | 2006158972 A | 6/2006 |
| JP | 2008537498 A | 9/2008 |
| JP | 2011092405 A | 5/2011 |
| JP | 2011523889 A | 8/2011 |
| JP | 2014511207 A | 5/2014 |
| JP | 2014521384 A | 8/2014 |
| KR | 100904142 B1 | 6/2009 |

(56) References Cited

FOREIGN PATENT DOCUMENTS

| | | |
|---|---|---|
| MD | 756 B1 | 7/1997 |
| MD | 756 C2 | 2/1998 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2008097781 A1 | 8/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2012058344 A1 | 5/2012 |
| WO | 2012099612 A1 | 7/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |
| WO | 2021050207 A1 | 3/2021 |

OTHER PUBLICATIONS

"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Catanese et al., "Measuring Sesamoid Position in Hallux Valgus: When is the Sesamoid Axial View Necessary," Foot and Ankle Specialist, 2014, 3 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Coetzee et al., "Revision Hallux Valgus Correction," Operative Techniques in Foot and Ankle Surgery, Section I, Chapter 15, 2011, pp. 84-96.
Coetzee et al., "The Lapidus Procedure: A Prospective Cohort Outcome Study," Foot & Ankle International, vol. 25, No. 8, Aug. 2004, pp. 526-531.
Collan et al., "The biomechanics of the first metatarsal bone in hallux valgus: A preliminary study utilizing a weight bearing extremity CT," Foot and Ankle Surgery, vol. 19, 2013, pp. 155-161.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
D'Amico et al., "Motion of the First Ray: Clarification Through Investigation," Journal of the American Podiatry Association, vol. 69, No. 1, Jan. 1979, pp. 17-23.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

(56) References Cited

OTHER PUBLICATIONS

Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Disease of the First Metatarsalphalangeal Joint," Podiatry Management, Jan. 2013, pp. 137-142.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
"Visionaire: Patient Matched Cutting Blocks Surgical Procedure," Smith & Nephew, Inc., 2009, 2 pages.
Vitek et al., "Die Behandlung des Hallux rigidus mit Cheilektomie und Akin-Moberg-Osteotomie unter Verwendung einer neuen Schnittlehre und eines neuen Schraubensystems," Orthopädische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Weber et al., "A Simple System for Navigation of Bone Alignment Osteotomies of the Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Wienke et al., "Bone Stimulation for Nonunions: What the Evidence Reveals," Podiatry Today, vol. 24, No. 9, Sep. 2011, pp. 52-57.
Wukich et al., "Hypermobility of the First Tarsometatarsal Joint," Foot and Ankle Clinics, vol. 10, No. 1, Mar. 2005, pp. 157-166.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics

(56) References Cited

OTHER PUBLICATIONS

LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
International Search Report and Written Opinion in PCT/US2022/030377, mailed date Aug. 10, 2022, 11 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Halluxvalgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
"Reconstructive Surgery of the Foot & Ankle," The Podiatry Institute, Update 2015, Conference Program, May 2015, 28 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

(56) References Cited

OTHER PUBLICATIONS

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Schon et al., "Cuneiform-Metatarsal Arthrodesis for Hallux Valgus," The Foot and Ankle, Second Edition, Chapter 8, 2002, pp. 99-117.

Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation of Metatarsal Fracture With Bone Plate in a Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

"Smith & Nephew scores a HAT-TRICK with its entry into the high-growth hammer toe repair market," Smith & Nephew, Jul. 31, 2014, 2 pages.

Sokoloff, "Lapidus Procedure," Textbook of Bunion Surgery, Chapter 15, 1981, pp. 277-287.

"Speed Continuous Active Compression Implant," BioMedical Enterprises, Inc., A120-029 Rev. 3, 2013, 4 pages.

Stableloc External Fixation System, Acumed, Product Overview, Effective date Sep. 2015, 4 pages.

Stahl et al., "Derotation of Post-Traumatic Femoral Deformities by Closed Intramedullary Sawing," Injury, vol. 37, No. 2, Feb. 2006, pp. 145-151, (Abstract Only).

DeCarbo et al., "Locking Plates: Do They Prevent Complications?," Podiatry Today, Apr. 2014, 7 pages.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Easley et al., "What is the Best Treatment for Hallux Valgus?," Evidence-Based Orthopaedics—The Best Answers to Clinical Questions, Chapter 73, 2009, pp. 479-491.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Eustace et al., "Hallux valgus, first metatarsal pronation and collapse of the medial longitudinal arch—a radiological correlation," Skeletal Radiology, vol. 23, 1994, pp. 191-194.

Fallin et al., US Provisional Application Entitled Indexed Tri-Planar Osteotomy Guide and Method, U.S. Appl. No. 62/118,378, filed Feb. 19, 2015, 62 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Fishco, "A Straightforward Guide to the Lapidus Bunionectomy," Podiatry Today, Retrieved online from <https://www.hmpgloballearningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

"Foot and Ankle Instrument Set," Smith & Nephew, 2013, 2 pages.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

"Futura Forefoot Implant Arthroplasty Products," Tornier, Inc., 2008, 14 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems für die Knieendoprothetik," Forschungsberichte, Technische Universitat Munchen, 165, 2002, 11 pages, including partial English Translation.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

Groves, "Operative Report," St. Tammany Parish Hospital, Date of Procedure, Mar. 26, 2014, 2 pages.

Hardy et al., "Observations on Hallux Valgus," The Journal of Bone and Joint Surgery, vol. 33B, No. 3, Aug. 1951, pp. 376-391.

"HAT-TRICK Lesser Toe Repair System," Smith & Nephew, Brochure, Aug. 2014, 12 pages.

"HAT-TRICK Lesser Toe Repair System, Foot and Ankle Technique Guide, Metatarsal Shortening Osteotomy Surgical Technique," Smith & Nephew, 2014, 16 pages.

(56) References Cited

OTHER PUBLICATIONS

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw, Surgical Technique," 2012, 16 pages.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

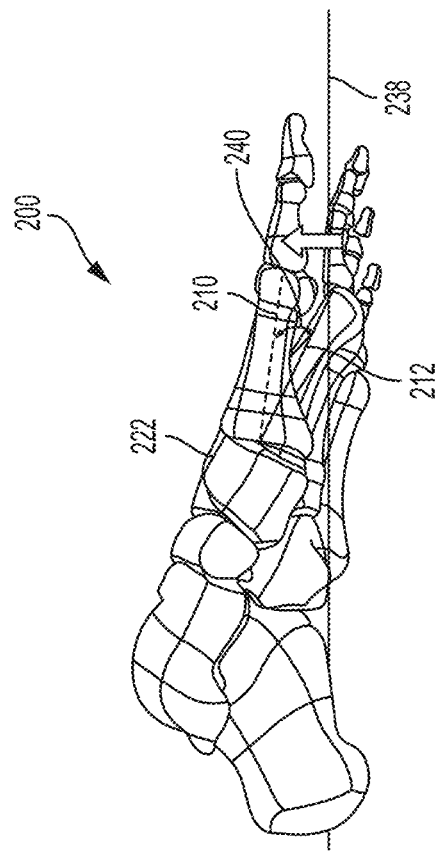
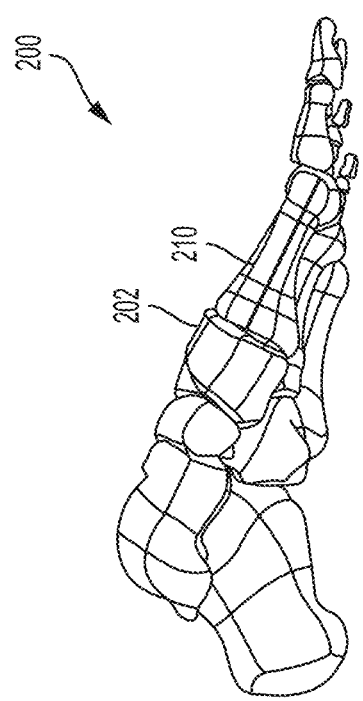
FIG. 3B
FIG. 3A

CUT GUIDE WITH INTEGRATED JOINT REALIGNMENT FEATURES

CROSS-REFERENCE

This application claims the benefit of U.S. Provisional Patent Application No. 63/246,792, filed Sep. 21, 2021, and U.S. Provisional Patent Application No. 63/190,787, filed May 20, 2021. The entire contents of each of these applications are incorporated herein by reference.

TECHNICAL FIELD

This disclosure relates to surgical devices and, more particularly, to surgical devices for assisting in bone cutting and/or realignment techniques.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is medially deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

SUMMARY

In general, this disclosure is directed to a combined bone cutting and joint realignment instrument that includes an integrated spacer body, bone preparation guide, and fulcrum body. The spacer body is configured to be inserted into a joint space between a metatarsal and an opposed cuneiform of a foot. The bone preparation guide body can be affixed to the spacer body with the spacer body extending downwardly from the bone preparation guide body. The bone preparation guide body can define at least one guide surface configured to be positioned over at least one of the metatarsal and the opposed cuneiform. The fulcrum body may be rotatably coupled to the spacer body within a bounded range of rotation, such as a bounded range of less than 45 degree. The fulcrum body can be configured to be inserted in an intermetatarsal space between the metatarsal and an adjacent metatarsal.

In practice, the combined bone cutting and joint realignment instrument can be used in a bone preparation and/or realignment procedure, such as a hallux valgus or bunion correction procedure performed on the first metatarsal of the foot. The spacer of the combination instrument may be inserted into the joint space between the first metatarsal and medial cuneiform. With the integrated bone preparation guide body attached thereto, the step of positioning the spacer body can simultaneously position one or more guide surfaces defined by the bone preparation guide over one or more bones (e.g., the metatarsal and/or cuneiform) to be prepared using the guide. In addition, the fulcrum body connected to the spacer body can be simultaneously positioned in the intermetatarsal space between the lateral side of the first metatarsal and medial side of an adjacent second metatarsal.

By configuring the combined instrument with a rotatable connection between the spacer body and fulcrum body, the clinician may have flexibility to manipulate the relative positions of the spacer body and fulcrum body, and bone preparation guide body associated therewith, relative to each other. For example, the spacer body may be freely rotatable relative to the fulcrum body within a bounded range of travel. This can establish a floppy connection between the two components, allowing the clinician to easily manipulate the position of the bone preparation guide body relative to one or more bones to be cut, e.g., causing the spacer body and fulcrum body to move relative to each other about the rotatable connection as the bone preparation guide body is moved. Further, by limiting the range of rotation between the spacer body and fulcrum body, the relative movement between the two components may be limited so the components do not get so far out of alignment with each other as to be challenging for the surgeon to work with the instrument.

To provide a combined instrument, the bone preparation guide body can be affixed to the spacer body and/or fulcrum body. For example, the bone preparation guide body can be permanently fabricated with the spacer body and/or fulcrum body (e.g., through casting, milling, machining, molding, 3D printing) to form a monolithic structure or fabricated separately and subsequently attached thereto to provide an integrated, unitary instrument comprised of inseparable features under normal use. In either case, the bone preparation guide body is affixed to the spacer body and/or fulcrum body so as to define a unitary instrument for use during a surgical procedure.

Providing a combined instrument having both spacer, fulcrum, and bone preparation guide functionalities can be exceptionally useful during a surgical procedure. Access to a patient's subcutaneous bone structure is typically limited by a comparatively small incision. Combining different functionalities into a unitary instrument can allow the instrument to be effectively and rapidly positioned through the small incision. Moreover, the surgeon and support staff have a limited number of hands with which to manipulate different tools and instruments used during the surgical procedure. Providing a combined instrument can allow a clinician to rapidly deploy the instrument during a surgical procedure, reducing the duration of the procedure and allowing more effective utilization of surgical resources.

The bone preparation guide body associated with the combined instrument can have a number of different forms. In general, the bone preparation guide body defines at least one guide surface positionable over a metatarsal and/or opposed cuneiform. A clinician can guide a tissue removal instrument along the guide surface (e.g., abutting the guide surface) to guide removal of an end portion of the metatarsal and/or opposed cuneiform. For example, the bone preparation guide body may define a first guide surface positionable over a metatarsal and a second guide surface positionable over the opposed cuneiform, with the two guide surfaces being separated from each other by a distance sufficient to span the tarsometatarsal joint. In various examples, the one or more guide surfaces include a facing guide surface to define a cutting slot there between.

In use, the clinician may position the bone preparation guide body over a dorsal surface of one or more bones to be prepared (e.g., a metatarsal and/or cuneiform). The clinician can then check the alignment of one or more guide surfaces defined by the bone preparation guide relative to the one or more bones to confirm the amount and/or orientation of bone to be removed (e.g., cut to be made) before making a cut. The clinician may perform this check visually with the unaided eye and/or through X-Ray imaging (fluoroscopy). The clinician can adjust the position of the combined instrument, particularly the bone preparation guide body, until the one or more guide surfaces are in a desired position and/or alignment. The clinician may insert one or more fixation pins through the bone preparation guide body to temporarily fixate the desired position before making one or more cuts using the guide body.

The bulk of the combination instrument, including spacer body, fulcrum body, and bone preparation guide body may have a tendency to obscure visualization (e.g., fluoroscopy) of the one or more guide surfaces relative to the underlying bones to be prepared using the bone preparation guide body. To reduce or eliminate this obscuring, the bone preparation guide body may be configured with a comparatively open framework. For example, the bone preparation guide body and/or guide surfaces defined by the body may be formed of comparatively thin-walled materials. This can allow the clinician to see around and/or through the walls of the bone preparation guide body (e.g., during imaging) to facilitate accurate aligning of the one or more guide surfaces relative to one or more bones to be cut. For example, the walls of the bone preparation guide body may have a thickness (e.g., in a proximal to distal direction along the length of the bone being cut when positioned over the dorsal surface of the bone) less than 2 mm, such as less than 1.5 mm, or less than approximately 1.0 mm (for example, ±10 percent).

In one example, a bone cutting and joint realignment instrument is described that includes a spacer body, bone preparation guide body, and fulcrum body. The spacer body is configured to be inserted into a joint space between a metatarsal and an opposed cuneiform of a foot. The bone preparation guide body is affixed to the spacer body with the spacer body extending downwardly from the bone preparation guide body. The bone preparation guide body defines at least one guide surface configured to be positioned over at least one of the metatarsal and the opposed cuneiform. The fulcrum body is rotatably coupled to the spacer body within a bounded range of rotation (e.g., less than 45 degrees). The fulcrum body is configured to be inserted in an intermetatarsal space between the metatarsal and an adjacent metatarsal.

The details of one or more examples are set forth in the accompanying drawings and the description below. Other features, objects, and advantages will be apparent from the description and drawings, and from the claims.

BRIEF DESCRIPTION OF DRAWINGS

FIGS. 3A and 3B are side views of a foot showing a normal first metatarsal position and an example sagittal plane misalignment position, respectively.

DETAILED DESCRIPTION

This disclosure is generally directed to a combined bone cutting and joint realignment instrument that includes an integrated spacer body, bone preparation guide, and fulcrum body. The spacer body is configured to be inserted into a joint space between a metatarsal and an opposed bone (e.g., cuneiform, cuboid) of a foot. The bone preparation guide body can be affixed to the spacer body with the spacer body extending downwardly from the bone preparation guide body. The bone preparation guide body can define at least one guide surface configured to be positioned over at least one of the metatarsal and the opposed cuneiform. The fulcrum body may be rotatably coupled to the spacer body, e.g., within a bounded range of rotation. The fulcrum body can be configured to be inserted in an intermetatarsal space between the metatarsal and an adjacent metatarsal.

The combined instrument can be used in a surgical procedure where one or more bone portions are to be prepared, such as a bone realignment procedure. Example procedures in which the combined instrument can be used include a bone alignment, osteotomy, fusion procedure, and/or other procedures where one or more bones are operated upon and/or realigned relative to one or more other bones. Such a procedure can be performed, for example, on bones (e.g., adjacent bones separated by a joint or different portions of a single bone) in the foot or hand, where bones are relatively smaller compared to bones in other parts of the human anatomy.

In one example, a procedure utilizing a combined instrument can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In other examples, a procedure utilizing a combined instrument can be performed to correct an alignment of a lesser metatarsal (e.g., second, third, four, or fifth metatarsal). As still a further example, a procedure utilizing a combined instrument can be performed as part of a metatarsal-phalange arthrodesis procedure to correct a relative position of a metatarsal and proximal phalanx across a metatarsophalangeal joint. While the example instruments of the disclosure are generally described as being useful for insertion into a space between opposed bone ends transitioning into an intermetatarsal space, the instruments may be used in any desired application and the disclosure is not limited in this respect.

Figure 1B:
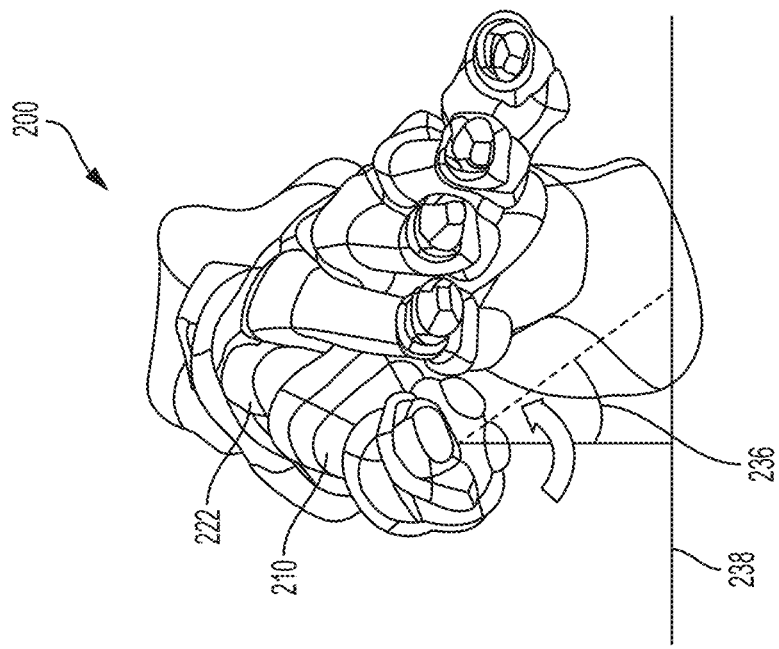
FIGS. 1A and 1B are front views of a foot showing a normal first metatarsal position and an example frontal plane rotational misalignment position, respectively.
Figure 1A:
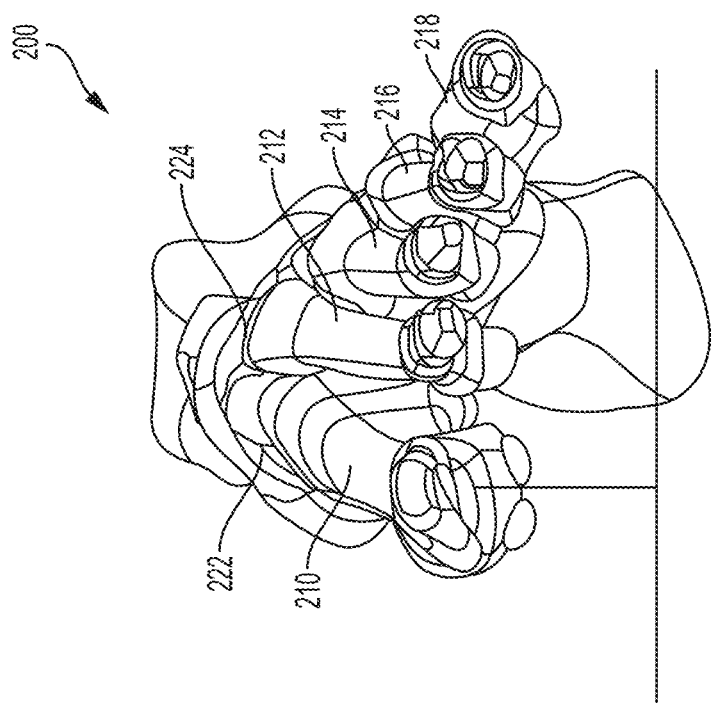
Figure 2B:
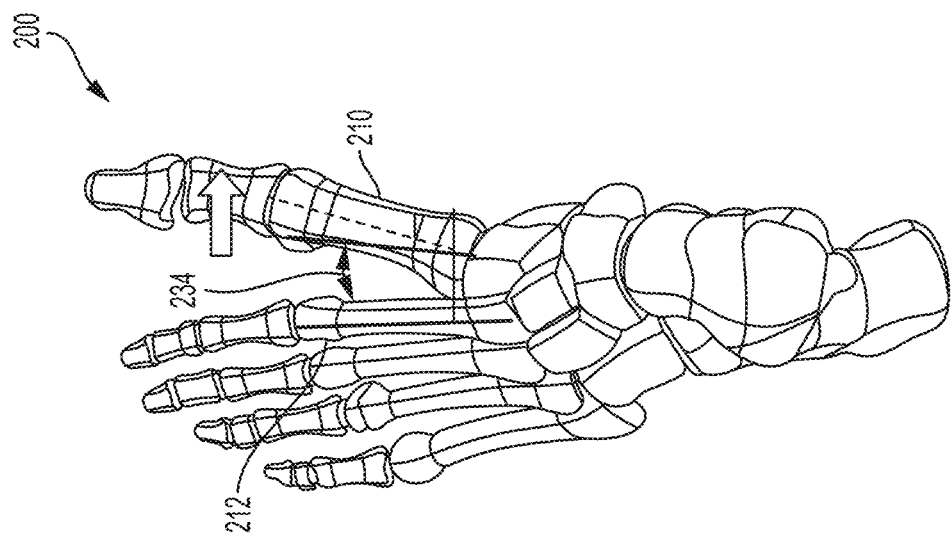
FIGS. 2A and 2B are top views of a foot showing a normal first metatarsal position and an example transverse plane misalignment position, respectively.
Figure 2A:
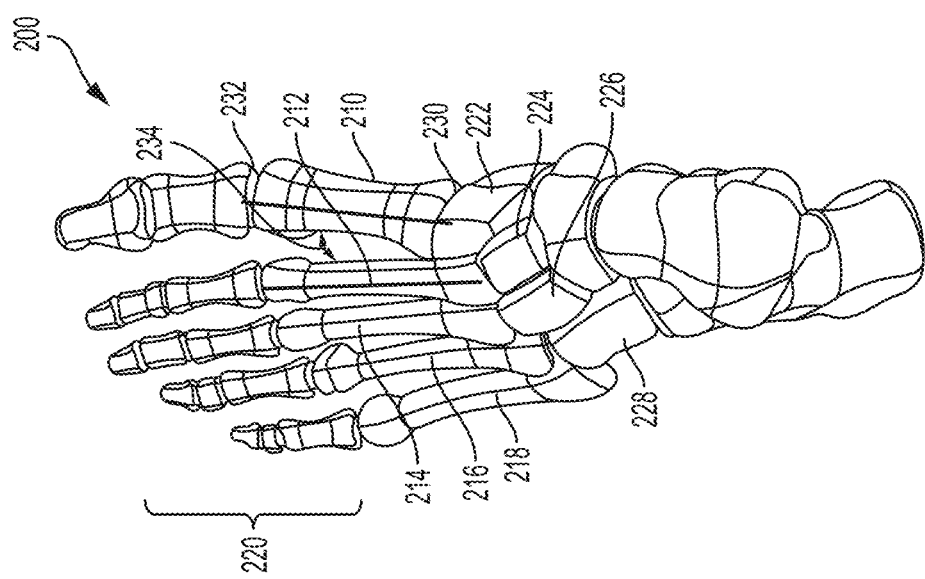

FIGS. 1-3 are different views of a foot 200 showing example anatomical misalignments that may occur and be corrected using a combined bone cutting and joint realignment instrument according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224, and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal ("MTP") joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A combined instrument according to the disclosure can define a spacer body extending a medial-to-lateral direction (e.g., parallel to the frontal plane) of the foot that is coupled to a fulcrum body extending in a proximal to distal direction (e.g., parallel to sagittal plane) of the foot. An integrally affixed bone preparation guide body may be carried by the spacer body such that the bone preparation guide body is positioned over one or more bones to be cut by positioning the spacer body in a joint space (e.g., TMT joint space) between a metatarsal and opposed cuneiform while the fulcrum body is simultaneously positioned in an intermetatarsal space between the metatarsal facing the spacer body and an adjacent metatarsal. The combined instrument can be used as part of a bone positioning technique to correct an anatomical misalignment of a bone or bones.

In some applications, the technique involves realigning a metatarsal relative to an adjacent cuneiform and/or adjacent metatarsal. The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal or portion thereof for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal.

In some applications, a combined instrument is used as part of a realignment technique to anatomically align first metatarsal 210 or a portion thereof by reducing the IMA from over 10 degrees to about 10 degrees or less (e.g., to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, a combined instrument is used as part of a realignment technique to anatomically align the metatarsal by reducing the metatarsal rotation from about 4 degrees or more to less than 4 degrees (e.g., to about 0 to 2 degrees) by rotating the metatarsal with respect to the medial cuneiform.

A combined instrument that defines a spacer body rotatably coupled to a fulcrum body and a bone preparation guide body integrally affixed to the instrument (e.g., to the spacer body and/or fulcrum body) according to the disclosure may be useful to provide a unitary structure (e.g., prior to or after being assembled) that can be positioned between two adjacent, intersecting joint spaces—a first joint space between opposed ends of a metatarsal and cuneiform and an inter-metatarsal space between adjacent metatarsals—and then used to cut one or both ends of the metatarsal and/or cuneiform defining the first joint space. The spacer body can include a portion insertable into the joint space to locate the bone preparation guide affixed thereto relative to the joint space and, correspondingly, the bones defining the joint space. The fulcrum body can establish and/or maintain space between adjacent bones being moved, e.g., helping to prevent lateral translation or base shift of the bones during rotation and/or pivoting.

For example, the combine instrument can include a spacer body positionable in the joint space between first metatarsal 210 and medial cuneiform 222 with a bone preparation guide body affixed thereto. The bone preparation guide body may include at least one guide surface, such as a cutting slot, positioned over an end of first metatarsal 210 and/or an end of medial cuneiform 222 to be cut, such as at least one metatarsal side guide surface (e.g., cutting slot) positionable over an end of first metatarsal 210 to be cut and at least one cuneiform side guide surface (e.g., cutting slot) positionable over an end of medial cuneiform 222 to be cut.

The combined instrument can also include a fulcrum body positionable in a joint space between first metatarsal 210 and second metatarsal 212. The fulcrum body can be inserted in the notch between first metatarsal 210 and second metatarsal 212 at the base of the metatarsals (e.g., adjacent respective cuneiforms) before moving the first metatarsal, e.g., to help avoid the proximal-most base of the first metatarsal 210 from shifting toward the proximal-most base of the second metatarsal 212. The fulcrum body can provide a point about which first metatarsal 210 can rotate and/or pivot while helping minimize or avoid base compression between the first metatarsal and the second metatarsal. In addition, use of the fulcrum body may cause first metatarsal 210 and medial cuneiform 222 to be better angled relative to one or more guide surfaces positioned over the end faces of the bones (one or more guide surfaces of the bone preparation guide body engaged with the spacer body), providing a better cut angle guided by the one or more guide surfaces than without use of the fulcrum body. This can help reduce or eliminate unwanted spring-back, or return positioning, of first metatarsal 210 after initial realignment of the metatarsal.

Figure 4A:
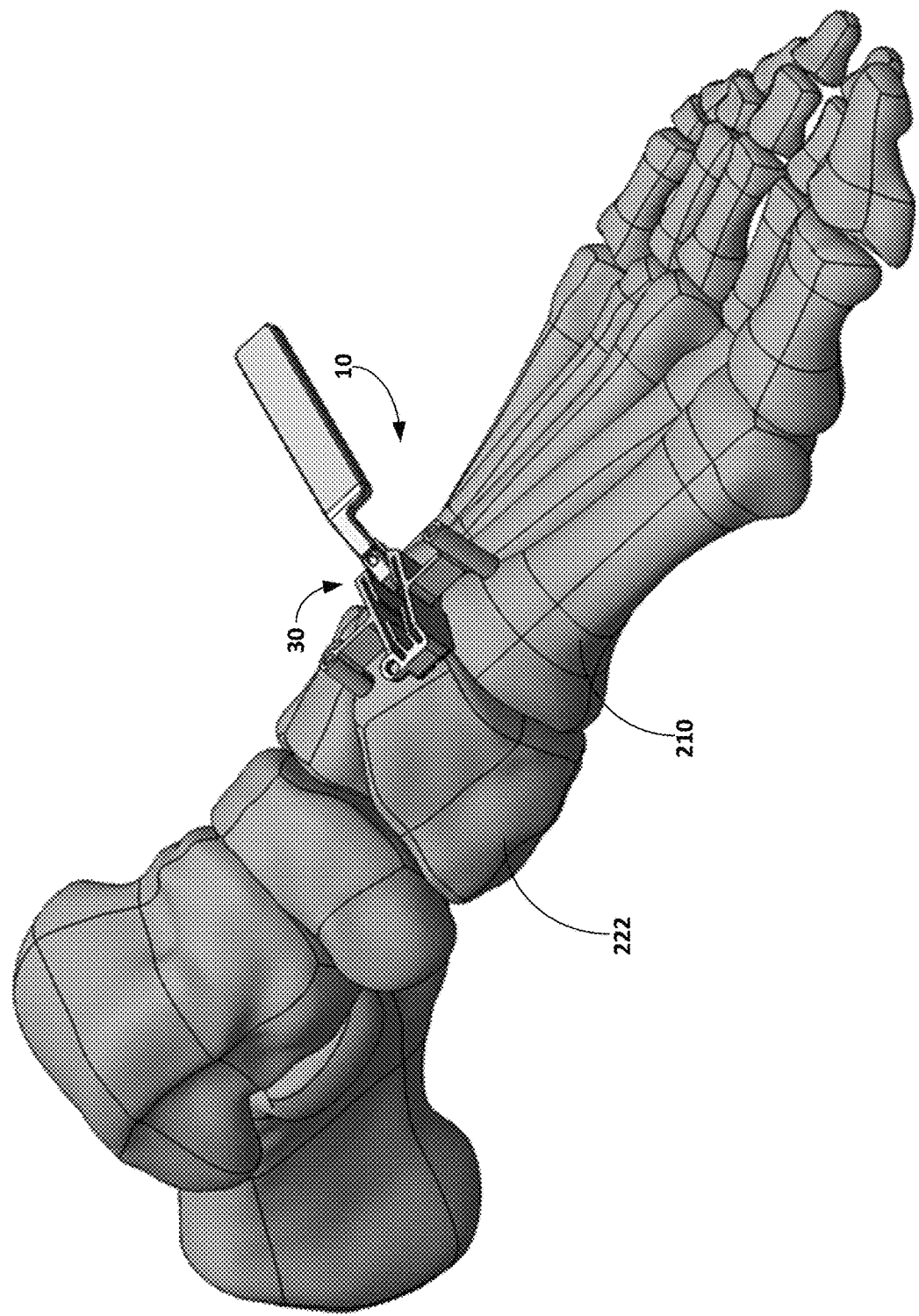
FIGS. 4A and 4B are perspective and top views, respectively, of an example bone positioning operation in which a combined instrument is positioned in a first joint space and an intersecting second joint space.
Figure 4B:
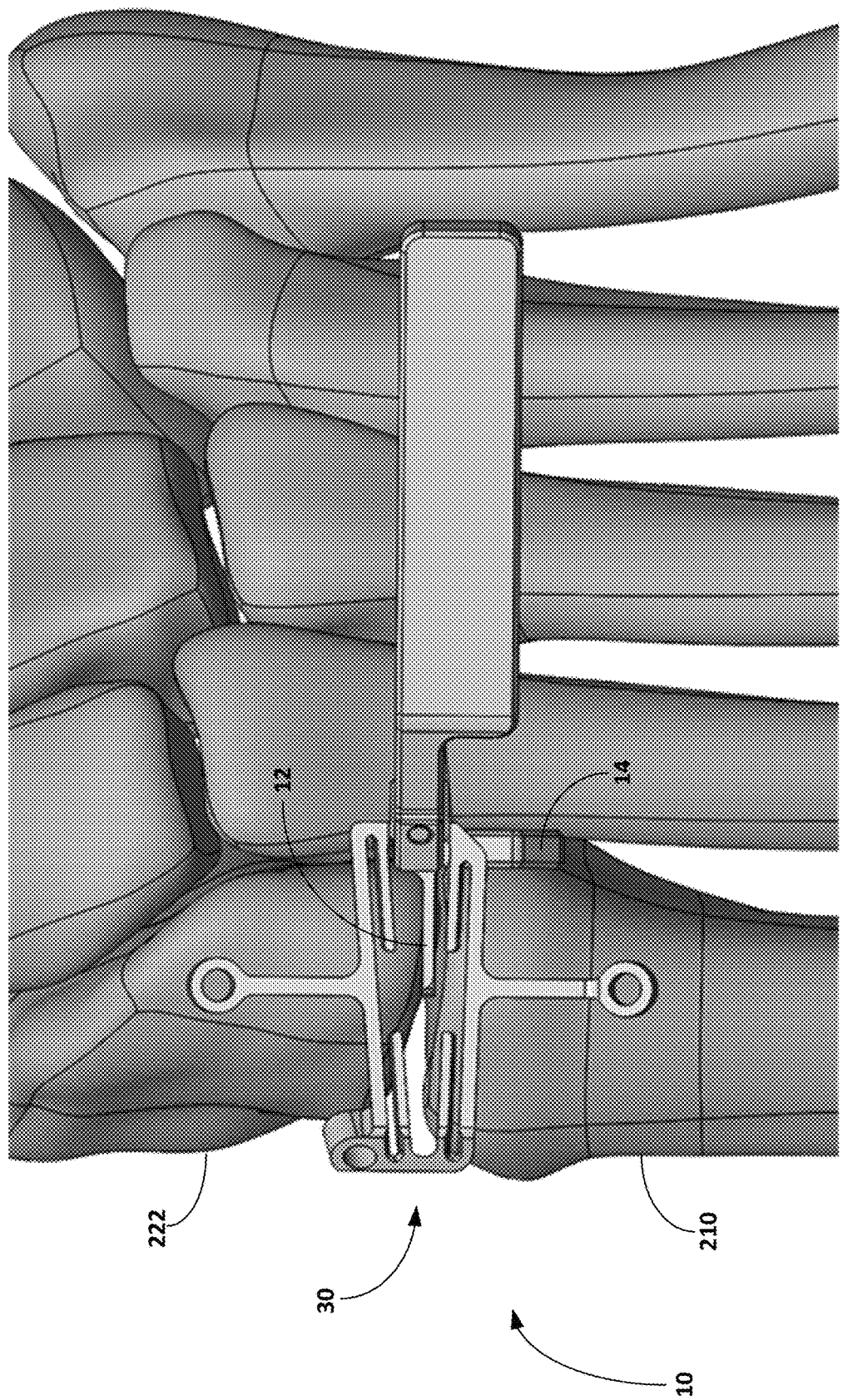

FIGS. 4A and 4B (referred to collectively as FIG. 4) are perspective and top views, respectively, of an example bone positioning operation in which a combined instrument 10 is positioned in a first joint space and an intersecting second joint space, where a bone forming the first and second joint spaces is being realigned relative to one or more adjacent bones. In particular, FIG. 4 illustrates a combined bone cutting and joint realignment instrument 10 having a spacer body 12 rotatably coupled to a fulcrum body 14 and a bone preparation guide body 30 affixed to the spacer body. Spacer body 12 is positioned at an intersection between an end of first metatarsal 210 and opposed medial cuneiform 222. Fulcrum body 14 is positioned between first metatarsal 210 and second metatarsal 212. Instrument 10 may optionally be used in conjunction with other surgical devices, such as a bone positioning guide that is operable to move first metatarsal 210 in one or more planes. Additional details on example bone positioning guides and related techniques are described in U.S. patent application Ser. No. 14/981,335, filed Dec. 28, 2015, and U.S. patent application Ser. No. 15/236,464, filed Aug. 14, 2016, the entire contents of which are incorporated herein by reference.

As shown in the example of FIG. 4, spacer body 12 can be positioned between opposed end of adjacent bones, such as opposed ends of a metatarsal (e.g., first metatarsal 210) and cuneiform (e.g., medial cuneiform 222) separated by a joint space. Spacer body 12 can define a length configured to be inserted into the joint space between the two bones, a thickness configured to extend between the metatarsal and the opposed cuneiform (e.g., with first metatarsal 210 and medial cuneiform 222 contacting opposed sides of the spacer body), and a width configured to extend in a medial to lateral direction across at least a portion of the joint space.

Spacer body 12 can be positioned at any suitable location across the joint space (e.g., in the front plane). In some examples, spacer body 12 extends across the entire width of the joint space between first metatarsal 210 and medial cuneiform 222, e.g., from a medial-most end of the joint space to a lateral-most end of the joint space. In other configurations, spacer body 12 extends across less than the entire width of the joint space, such as a lateral-most half or less of the joint space, or a lateral-most quarter or less of the joint space.

In some configurations, spacer body 12 has a length (in the dorsal to plantar direction) sufficient such that, when the spacer body is inserted into the joint space, the spacer body projects dorsally above the joint space. In other configurations, spacer body 12 may be comparatively smaller such that, when the spacer body is inserted into the joint space, the top edge of the spacer body is flush with or recessed relative to the dorsal-most surface of first metatarsal 210 and/or medial cuneiform 222 at the joint. This latter configuration can be useful to help prevent spacer body 12 from visually obstructing the joint space.

Bone preparation guide body 30 may affixed to spacer body 12 to define a unitary/integral instrument. The positioning of spacer body 12 in the joint space can dictate the positioning of bone preparation guide body 30 coupled thereto and, correspondingly, the guiding of a bone preparation instrument facilitated by the bone preparation guide.

Combined instrument 10 also includes fulcrum body 14. In use, the clinician can insert fulcrum body 14 between first metatarsal 210 and second metatarsal 212 (or other adjacent bones, when not performing a metatarsal realignment) concurrent with inserting spacer body 12 into the TMT joint space between first metatarsal 210 and medial cuneiform 222. For example, the clinician can insert spacer body 12 in the joint space between first metatarsal 210 and medial cuneiform 222 and also insert fulcrum body 14 in the joint space between first metatarsal 210 and second metatarsal 212 at the same time. Bone preparation guide body 30 affixed to instrument 10 is positioned over a dorsal side of first metatarsal 210 and/or medial cuneiform 222 concurrently upon insertion of the spacer body and fulcrum body into respective joint spaces.

Figure 5A:
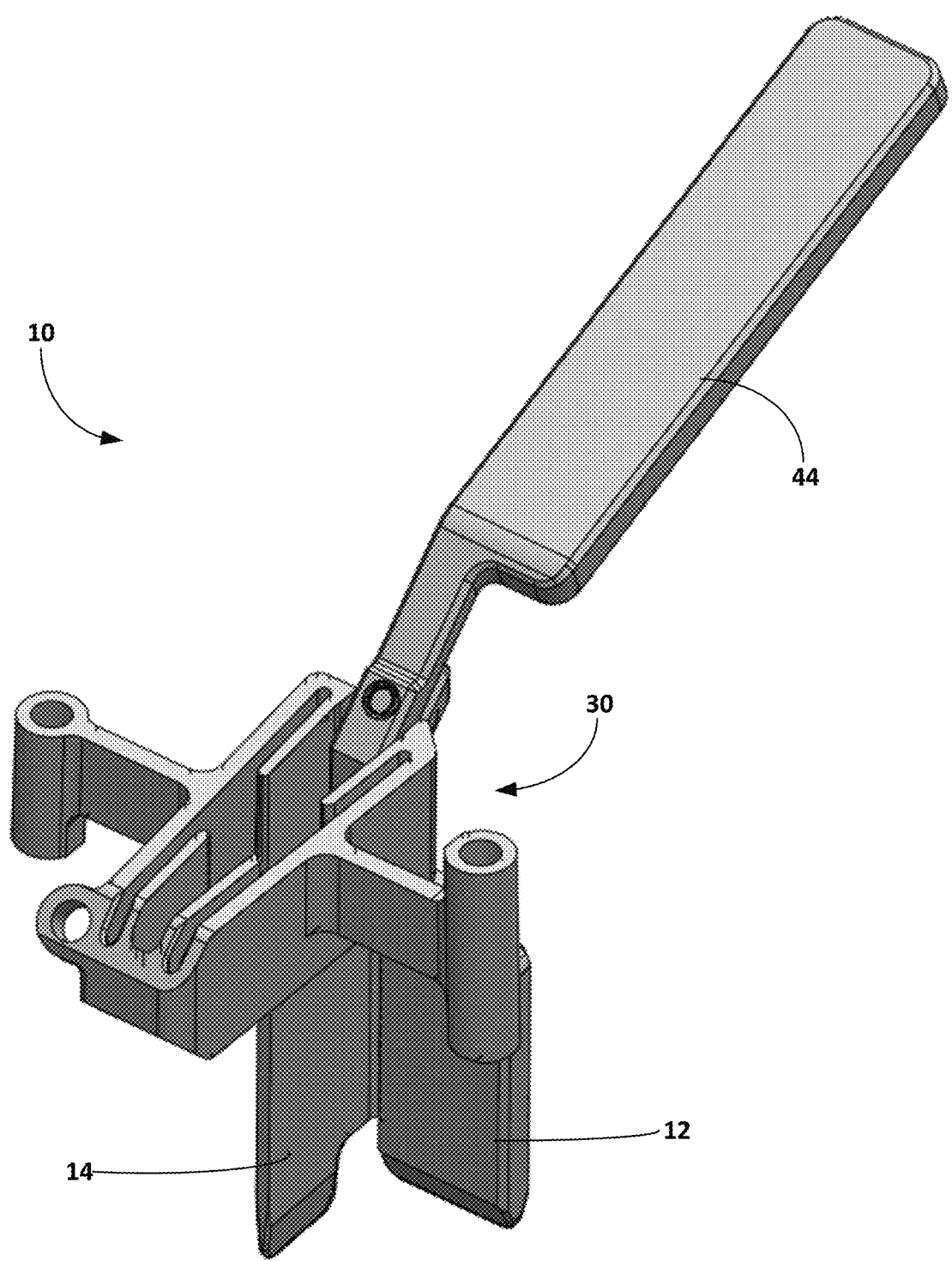
FIGS. 5A and 5B are perspective and top views, respectively, of an example configuration of a combined instrument.
Figure 5B:
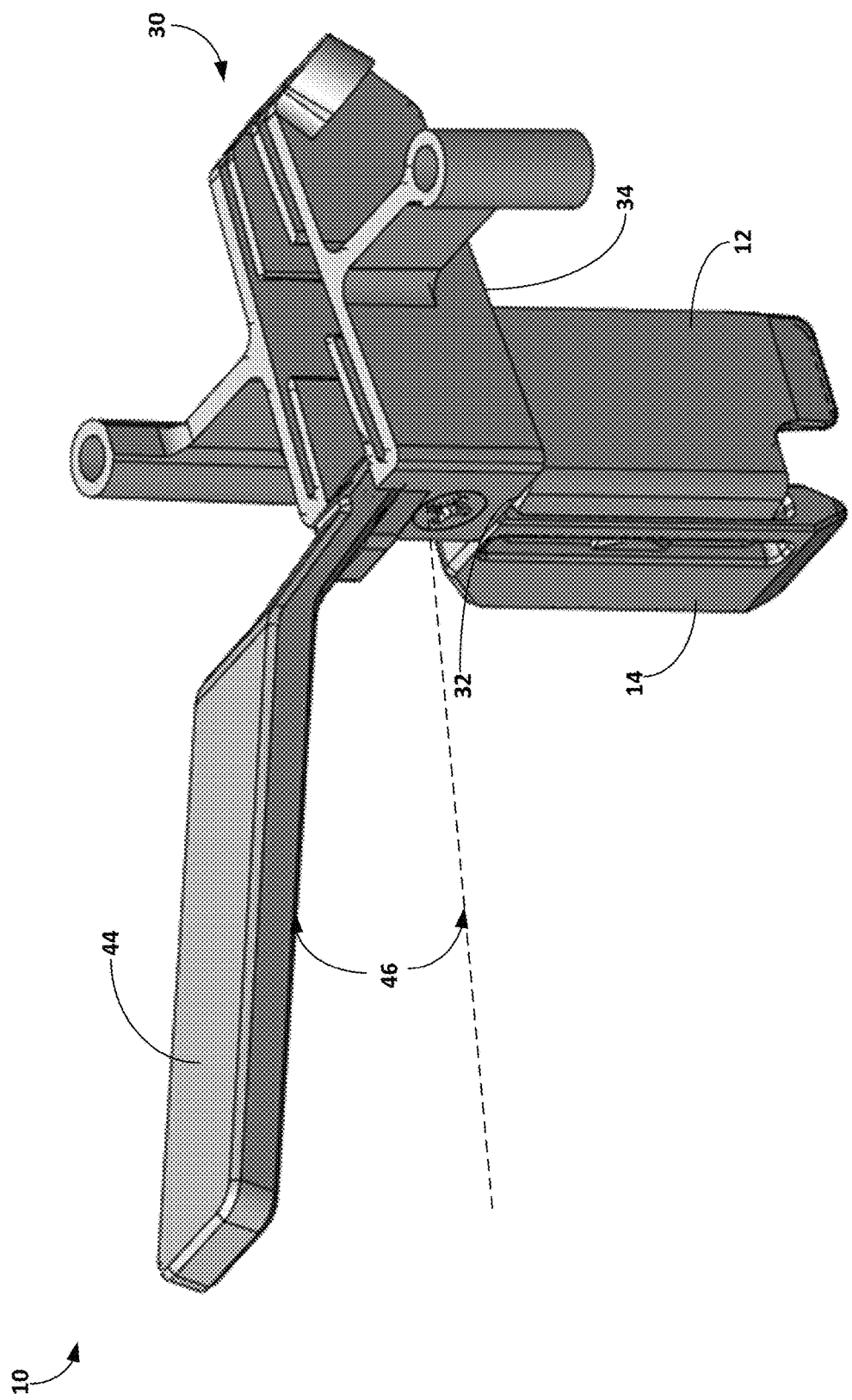

FIGS. 5A and 5B (collectively referred to as FIG. 5) are perspective and top views, respectively, of an example configuration of combined instrument 10. As shown in this example, instrument 10 includes bone preparation guide body 30 affixed to spacer body 12 and spacer body 12 rotatably coupled to fulcrum body 14.

In general, spacer body 12 may define a length configured to be inserted into the joint space, a thickness configured to extend between the bones defining the joint space (e.g., metatarsal 210 and opposed cuneiform 222), and a width configured to extend in a medial to lateral direction partially or fully across the joint space. Spacer body 12 can have a length extending from a top end to a bottom end. In some examples, bone preparation guide body 30 is affixed to spacer body 12 such that the top end of the spacer body is approximately coplanar with or located vertically below the bottom end of the bone preparation guide body (e.g., the bottom end of at least one guide surface of the bone preparation guide body). For example, as shown in FIG. 5, a top surface 32 of spacer body 12 may be coplanar with or recessed relative to a bottom edge 34 of bone preparation guide body 30.

Fulcrum body 14 can define a length configured to be inserted into the intermetatarsal space, a thickness configured to extend between first metatarsal 210 and second metatarsal 212, and a width configured to extend in the proximal to distal direction across the foot. The thickness of fulcrum body 14 may be substantially constant across the length of the fulcrum body or may be tapered toward the leading end to facilitate insertion of fulcrum body 14 into a space between adjacent metatarsals. In general, fulcrum body 14 may have a width that extends partially within the intermetatarsal space between first metatarsal 210 and second metatarsal 212. When inserted into the intermetatarsal space, fulcrum body 14 may extend from the base (e.g., proximal-most end) of first metatarsal 210 toward the distal-most end of the first metatarsal a distance less than half the length of the metatarsal, such as a distance less than a quarter of the length of the metatarsal, a distance less than 10% of the length of the metatarsal, or a distance less than 5% of the length of the metatarsal.

In some examples, instrument 10 includes a handle 44. Handle 44 can be operatively connected to and extend from bone preparation guide body 30. By connecting handle directly to bone preparation guide body 30, the clinician may more easily manipulate the location of one or more guide surfaces defined by bone preparation guide body 30 than if the handle is attached to another portion of instrument 10. Handle 44 may be any structure projecting from bone preparation guide body 30 of instrument 10 that can provide a gripping location for the instrument during use.

In some examples, such as the example illustrated in FIG. 5, handle 44 can project angularly away from bone preparation guide body 30 to define a tissue retraction space 46. The tissue retraction space may be a region bounded on one side by bone preparation guide body 30 and one side of handle 44. In use, combined instrument 10 may be inserted into an incision space with handle 44 extending out of the surgical incision and over an epidermal layer with tissue captured in the tissue retraction space. For example, combined instrument 10 may be inserted into an intermetatarsal space with handle 44 projecting toward the lateral side of the foot being operated upon. The tissue retraction space may help retract tissue and push the tissue laterally away from a first metatarsal and/or medial cuneiform being operated upon. In other configurations, however, handle 44 may extend at a different direction (e.g., straight upwardly or dorsally from the bone preparation guide body) and/or be attached to a different portion of instrument 10 (e.g., fulcrum body 14) then bone preparation guide body 30. In still other configurations, instrument 10 may not include a handle 44.

Fulcrum body 14 is operatively coupled to spacer body 12. In some configurations, fulcrum body 14 is fixedly coupled to spacer body 12 to form a permanent, unmovable connection between the fulcrum body and spacer body. In other examples, however, fulcrum body 14 may be movably coupled to spacer body 12 such that the fulcrum body is rotatable relative to the spacer body. Configuring fulcrum body 14 to be relatively rotatable to spacer body 12 can be useful to allow the angle between the fulcrum body and spacer body to be changed or manipulated by the clinician to accommodate different patient anatomies and conditions that may be encountered during a particular surgical procedure.

In some implementations, fulcrum body 14 is rotatably coupled to spacer body 12 within a bounded range of rotation. That is, fulcrum body 14 may be mechanically coupled to spacer body 12 to provide a unitary instrument but may be rotatable relative to the spacer body within a constrained or limited range of rotation. Limiting the range of rotation between fulcrum body 14 and spacer body 12 can be beneficial to allow some relative movement between the spacer body and fulcrum body but not providing too much relative rotation such that the fulcrum body becomes overly floppy or difficult for the clinician to manipulate during a surgical procedure.

Figure 6A:
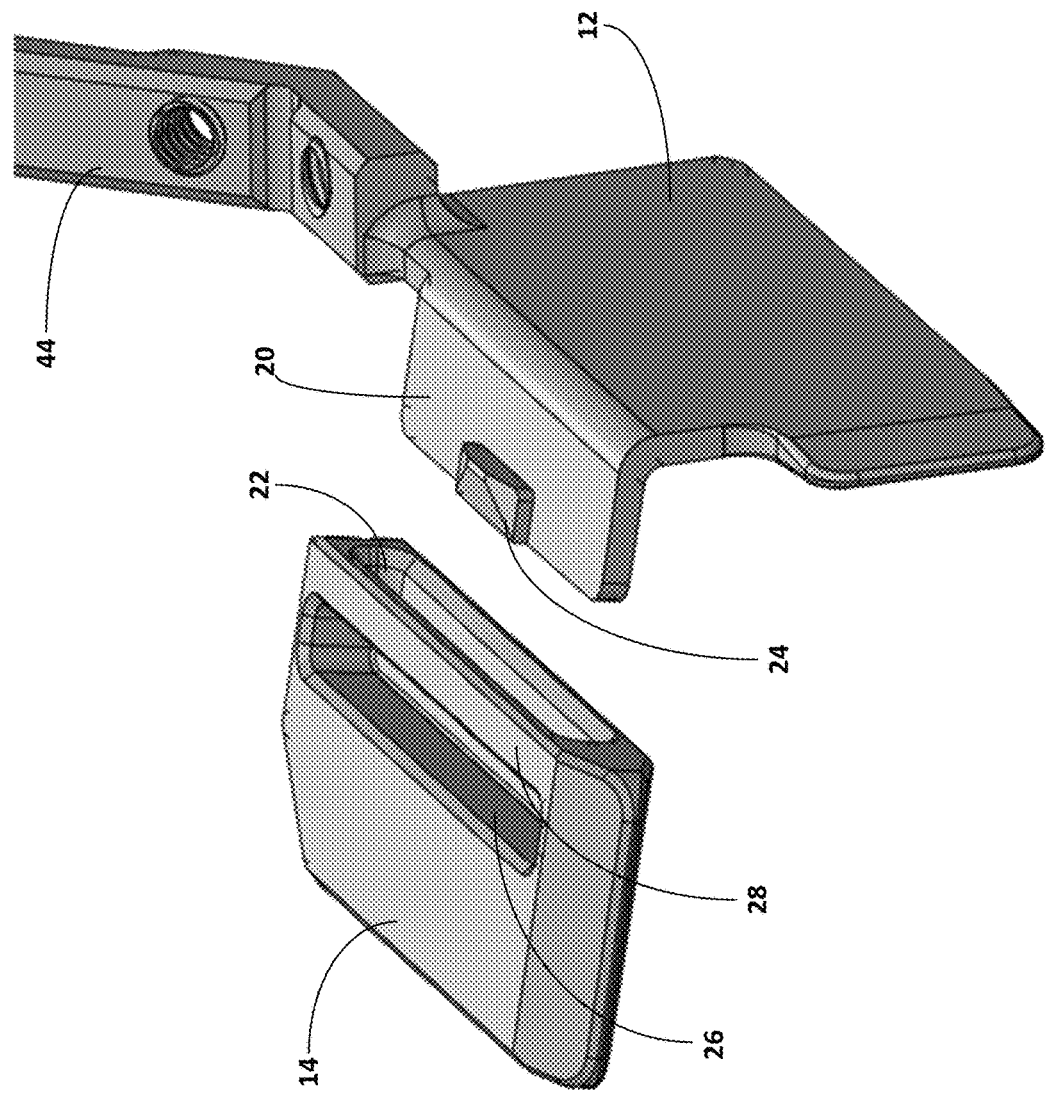
FIGS. 6A and 6B illustrate one example coupling arrangement that can be used to connect a spacer body to a fulcrum body on a combined instrument according disclosure.
Figure 6B:
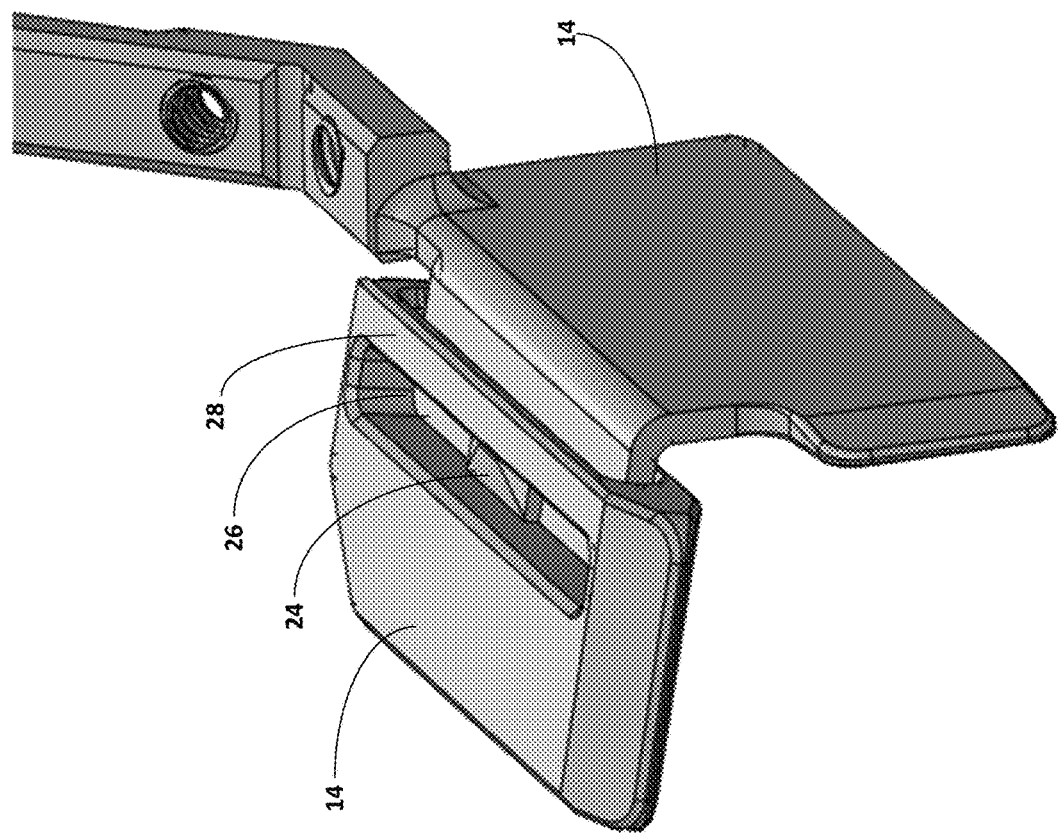

While various coupling arrangements may be used to operatively connect fulcrum body 14 to spacer body 12, FIGS. 6A and 6B (collectively referred to as FIG. 6) illustrate one example coupling arrangement that can be used to connect a spacer body to a fulcrum body on a combined instrument according disclosure. As shown in the illustrated example, a complementary connection between fulcrum body 14 and spacer body 12 can be provided in which one of the fulcrum body and spacer body has a projecting tongue 20 and the other of the fulcrum body and the spacer body has a corresponding receiving groove 22 into which the projecting tongue 20 can be inserted. Projecting tongue 20 can extend at an angle relative to the plane defined by the widthwise direction of fulcrum body 14 or spacer body 12, such as an angle approximately orthogonal (e.g., 80° to 100°, such as 85° to 95°, or from 88° to 92°, or 90°) to the plane defined by the widthwise direction of the fulcrum body or spacer body.

In the illustrated arrangement, projecting tongue 20 is illustrated as extending orthogonally from spacer body 12. When spacer body 12 is positioned in a tarsometatarsal joint space extending in a medial-to-lateral direction, projecting tongue 20 may extend in a proximal-to-distal direction in the intermetatarsal space between first metatarsal 210 and second metatarsal 212. Projecting tongue 20 may have a width (e.g., in the proximal-to-distal direction when inserted into the joint) less than the width of spacer body 12, such as a width less than or equal to three quarters the width of the spacer body, less than or equal to half the width of the spacer body, or less than or equal to one fifth of the width of the spacer body.

Receiving groove 22 can define an opening into which projecting tongue 20 can be inserted. Receiving groove 22 is illustrated as extending in the widthwise direction across a portion of the width of fulcrum body 14. When so configured, receiving groove 22 can extend in the proximal-to-distal direction in the intermetatarsal space between first metatarsal 210 and second metatarsal 212, when fulcrum body 14 is inserted into the metatarsal space.

Receiving groove 22 can define an opening cross-sectional size larger than a cross-sectional size of projecting tongue 20 to allow the tongue to rotate relative to the groove.

To retain projecting tongue 20 in receiving groove 22, one of the tongue and the groove can include a locking projection 24 and the other of the tongue and the groove can include a complementary locking receiving cavity 26.

For example, the locking projection 24 may extend outwardly from a face of the projecting tongue, and the complementary locking receiving cavity 26 may extends through a wall surface of the other of the spacer body and the fulcrum body defining the groove. Locking receiving cavity 26 may be configured (e.g., sized and/or shaped) for locking projection 24 to extend partially or fully into and/or through the locking receiving cavity 26.

Locking projection 24 may be a region of thicker material extending perpendicularly outwardly relative to the face of projecting tongue 20 (e.g., in a direction perpendicular to the width and length of the projecting tongue). Locking projection 24 can have any polygonal or arcuate shape and, in some examples, may have a tapered profile from a comparatively narrower end advanced in a leading direction into receiving groove 22 to a comparatively wider end advanced in a trailing direction into the receiving groove.

When locking projection 24 extends generally perpendicularly relative to the face of projecting tongue 20 (e.g., defining a portion of increased thickness), locking receiving cavity 26 may define an opening extending through a wall surface that is perpendicular to the wall surface defining receiving groove 22. In some examples, a beam 28 extends between top and bottom wall surfaces of fulcrum body 14, bounding receiving groove 22 on one side and locking receiving cavity 26 on another side. Beam 28 may be sufficiently thin and/or flexible so as to elastically bend upon insertion of projecting tongue 20 into receiving groove 22 and then returned to an unbent shape to retain locking projection 24 in locking receiving cavity 26.

While the foregoing discussion of a rotatable connection between spacer body 12 and fulcrum body 14 has focused on a configuration in which projecting tongue 20 is formed on spacer body 12 and receiving groove 22 is defined on fulcrum body 14, projecting tongue 20 may alternatively extend from fulcrum body 14 and receiving groove 22 be defined by spacer body 12. Other examples of rotatable connections that may be used include a hinged connection between spacer body 12 and fulcrum body 14, e.g., with stops built in that limit the range of rotation between the spacer body and fulcrum body.

Figure 7B:
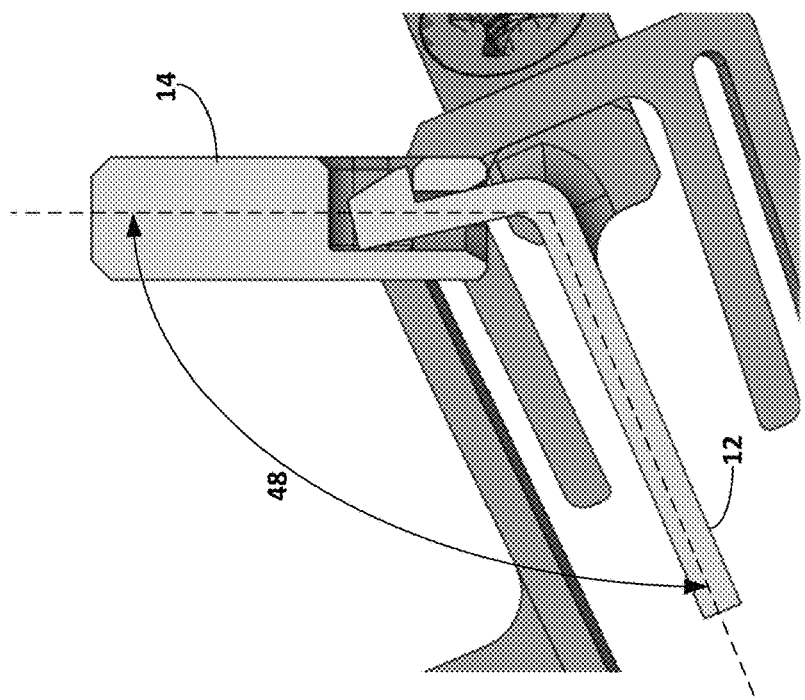
FIGS. 7A and 7B are top sectional views of a combined instrument showing example bounded rotational positions to which a fulcrum body and a spacer body can rotate.
Figure 7A:
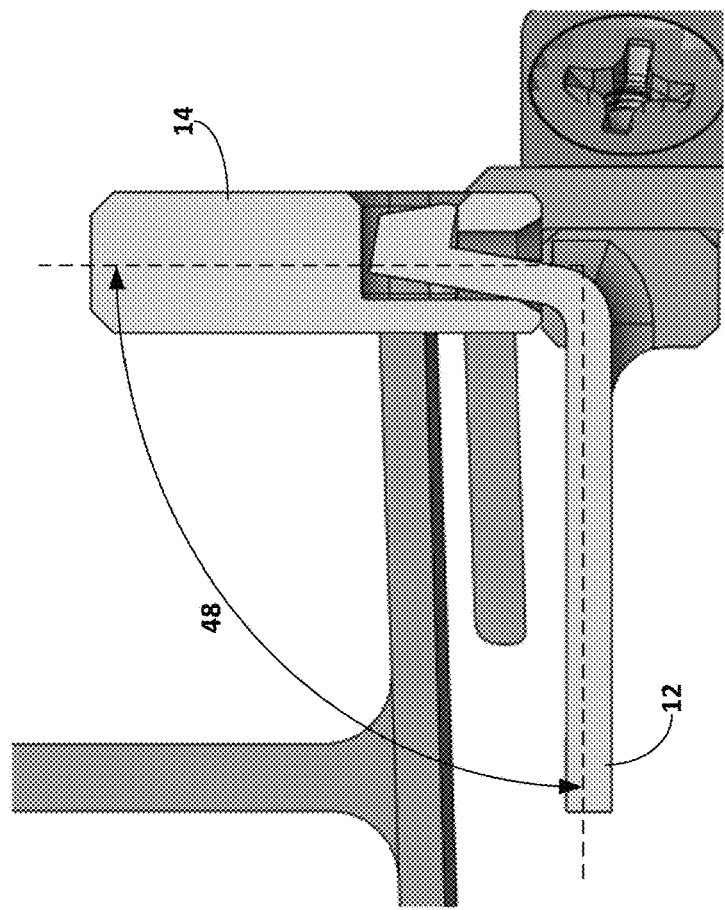

FIGS. 7A and 7B (collectively referred to as FIG. 7) are top sectional views of combined instrument 10 showing example bounded rotational positions to which fulcrum body 14 and spacer body 12 can rotate. FIG. 7 illustrates a combined instrument 10 utilizing the complementary connection features between spacer body 12 and fulcrum body 14 illustrated and described with respect to FIG. 6. However, the relative rotational positions and angles illustrated and described with respect to FIG. 7 may be achieved using other bounded rotational connection configurations between spacer body 12 and fulcrum body 14.

As shown in FIG. 7, spacer body 12 and fulcrum body 14 can define an angle of 48 between a plane defined by the widthwise extent of the spacer body and a plane defined by the widthwise extent of the fulcrum body. FIG. 7A illustrates a rotational position between spacer body 12 and fulcrum body 14 defining an example minimum intersection angle 48. FIG. 7B illustrates an rotational position between spacer body 12 and fulcrum body 14 defining an example maximum intersection angle 48. As shown in these examples, the amount of angular rotation between spacer body 12 and fulcrum body 14 may be controlled by the size of locking projection 24 and the corresponding size (e.g., depth) of locking receiving cavity 26.

In some examples, spacer body 12 and fulcrum body 14 are configured to rotate relative to each other to allow the angular intersection 48 between the two bodies to vary within a from 80 degrees to 125 degrees, optionally including all sub-ranges therein. In some examples, spacer body 12 and fulcrum body 14 are rotatably coupled together to allow angle 48 to adjust from a minimum of approximately 90 degrees (e.g., ±10%) to a greater angle. For example, spacer body 12 and fulcrum body 14 may be rotatably coupled together to allow angle 48 to adjust from a minimum of approximately 90 degrees to 120 degrees or less. For instance, in certain implementations, spacer body 12 and fulcrum body 14 may be rotatably coupled together to allow angle 48 to vary within a bounded range of rotation of approximately ±45° or less, such as ±35° or less, ±30° or less, ±25° or less, ±15° or less, or ±10° or less. The absolute value of angle 48 may be within a range from 90° to 115°, optionally including all sub-ranges therein.

In some examples, instrument 10 (e.g., spacer body 12, fulcrum body 14, bone preparation guide body 30) will be formed as a unitary structure, e.g., by milling, casting, or molding the components to be permanently and structurally integrated together. In other examples, one or more the features may be fabricated as separate components that are subsequently joined together. For example, bone preparation guide body 30 may be formed integrally with spacer body 12 and/or fulcrum body 14, or may be formed separately from one or both bodies and subsequently fixedly coupled thereto to form a unitary. For example, in different configurations, bone preparation guide body 30 can be welded, bolted, and/or adhesively affixed to spacer body 12 and/or fulcrum body 14 to form a fixed connection between the bone preparation guide body and the spacer body and/or fulcrum body. In either case, spacer body 12, fulcrum body 14, bone preparation guide body 30 may be mechanically interconnected so as to be inseparable during use in a surgical procedure.

In some configurations, bone preparation guide body 30 may be attached to spacer body 12 and/or fulcrum body 14 via a sliding connection. For example, a top end of spacer body 12 may define a rail extending parallel to the widthwise direction of the spacer body. Bone preparation guide body 30 can be mounted on the rail so as to be movable (e.g., slidable) in the medial-to-lateral direction (e.g., parallel to the widthwise direction of spacer body 12). A set screw or other locking feature can be used to lock a specific position of the bone preparation guide body 30 relative to spacer body 12. For example, bone preparation guide body 30 may be operatively connected to an adjuster (e.g., an adjustment knob). The clinician can manipulate the adjuster to control the position of bone preparation guide body 30.

Configuring bone preparation guide body 30 to be movable relative to spacer body 12 and/or fulcrum body 14 can be useful to allow the clinician to move one or more guide surfaces defined by the bone preparation guide body relative to one or more target bones to be cut. This can allow the position of the one or more guide surfaces to be moved depending on the specific anatomy encountered by the clinician during a procedure. The clinician can move the one or more guide surfaces within a bounded range of travel while still having a single, unitary instrument 10 (e.g., optionally graspable by a single handle/hand of the clinician). For example, during the surgical procedure, the clinician may insert combined instrument 10 into joint spaces of the foot, positioning one or more guide surfaces of bone preparation guide body 30 over metatarsal 210 and/or cuneiform 222. The clinician may then adjust the position of bone preparation guide body 30 relative to spacer body 12, e.g., by adjusting the medial-most end of the guide surface to be over the medial-most side of the bone to be cut and/or the lateral-most end of the guide surface to be over the lateral-most side of the bone to be cut. For example, the clinician may position the medial-most end of the guide surface be at or medially-past the medial side of the bone to be cut and/or position lateral-most end of the guide surface be at or lateral-past the lateral side of the bone to be cut. This can position the guide surface so that a bone preparation instrument guided by the guide surface cuts across the entire width of the bone to be cut.

Figure 8B:
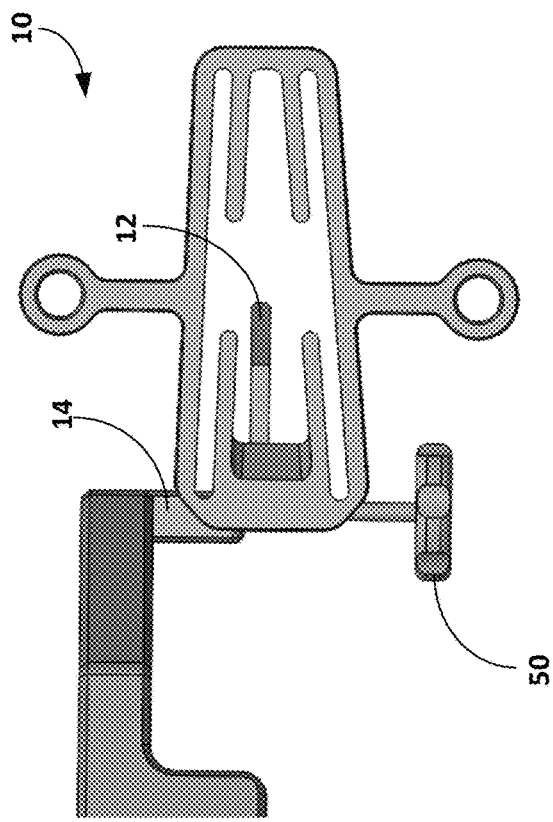
FIGS. 8A and 8B illustrate two example configurations of a combined instrument including an actuator/locking feature.
Figure 8A:
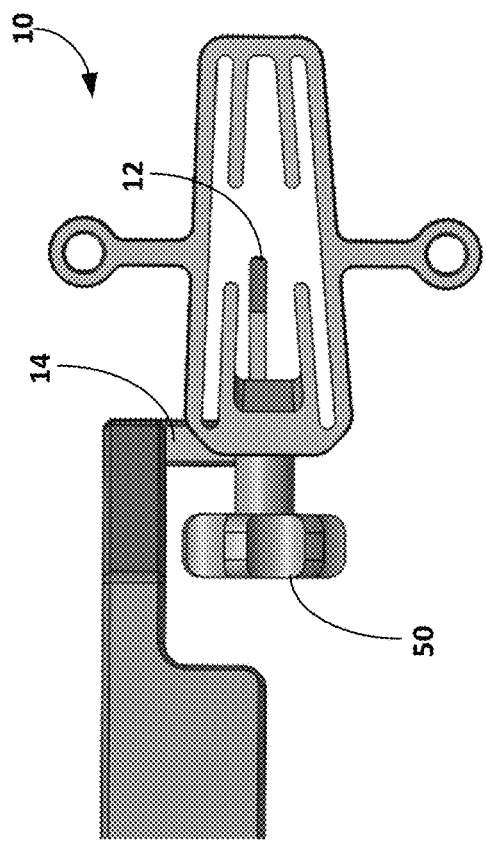

FIGS. 8A and 8B illustrate two example configurations of instrument 10 including an actuator 50. Actuator 50 is illustrated as extending parallel to spacer body 12 in the example of FIG. 8A and perpendicular to spacer body 12 in the example of FIG. 8B. Actuator 50 may be implemented using a screw, knob, ratchet, a gear, and/or other mechanism. Actuator 50 may be configured to move bone preparation guide body 30 relative to spacer body 12 or, in other examples, may merely function to hold a moved position of the bone positioning guide body relative to the spacer body (e.g., with the bone positioning guide body being moved by the hand the clinician and then locked in place using the actuator or locking feature 50).

In some examples, instrument 10 is used as part of a metatarsal realignment procedure in which a metatarsal is realigned relative to an adjacent cuneiform and/or metatarsal in one or more planes, such as two or three planes. Additional details on example bone realignment techniques and devices with which instrument 10 may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018, and US Patent Publication No. 2017/0042599 titled "TARSAL-METATARSAL JOINT PROCEDURE UTILIZING FULCRUM," filed on Aug. 14, 2016. The entire contents of each of these documents are hereby incorporated by reference.

With further reference to FIG. 4, bone preparation guide body 30 is illustrated as extending from a first end positioned over first metatarsal 210 to a second end positioned over medial cuneiform 222. One or both ends of the body can define one or more fixation apertures configured to receive fixation pin(s) for securing bone preparation guide body 30 to one or more bones.

Bone preparation facilitated by bone preparation guide body 30 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing instrument 10, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position. In still other applications, the end of one of the moved bone and the other bone is prepared before moving the bone into the aligned position while the end of the opposite facing bone (either the moved bone or the other bone) is prepared after moving the bone into the aligned position.

Movement of one bone relative to another bone can be accomplished using one or more instruments and/or techniques. In some examples, bone movement is accomplished using a bone positioning device, e.g., that applies a force through one or more moving components to one bone, causing the bone to translate and/or rotate in response to the force. This may be accomplished, for example, using a bone positioning guide that includes a bone engagement member, a tip, a mechanism to urge the bone engagement member and the tip towards each other, and an actuator to actuate the mechanism. Additionally or alternatively, bone movement may be accomplished using a compressor-distractor by imparting movement to one bone relative to another bone as the compressor-distractor is positioned on substantially parallel pins, causing the pins to move out of their substantially parallel alignment and resulting in movement of the underlying bones in one plane (e.g., frontal plane, sagittal plane, transverse plane), two or more planes, or all three planes. As yet a further addition or alternative, a clinician may facilitate movement by physically grasping a bone, either through direct contact with the bone or indirectly (e.g., by inserting a K-wire, grasping with a tenaculum, or the like), and moving his hand to move the bone.

When used, the clinician can insert instrument 10 between first metatarsal 210 and second metatarsal 212 and between first metatarsal 210 and medial cuneiform 222 (or other adjacent bones, when not performing a first metatarsal realignment) at any time prior to moving the first metatarsal (e.g., by actuating a bone positioning guide or otherwise manipulating the bone). In one embodiment, the clinician prepares the joint being operated upon to release soft tissues and/or excise the plantar flare from the base of the first metatarsal 210. Either before or after installing an optional bone positioning guide over adjacent bones, the clinician inserts the instrument 10 at the joint between the first metatarsal and the second metatarsal and at the joint between the first metatarsal and medial cuneiform. The clinician can adjust the angular position of fulcrum 12 relative to spacer 14 within the bounded range of rotation set by the instrument before, during, and/or after inserting instrument 10 into the joint spaces. In either case, the clinician can subsequently actuate a bone positioning guide (e.g., when used). As distal portion of first metatarsal can move toward the second metatarsal in the transverse plane to close the IMA, thereby pivoting a proximal portion of the first metatarsal about fulcrum body 14 and reducing the IMA between the first metatarsal and the second metatarsal. The use of fulcrum body 14 can minimize or eliminate base compression between adjacent bones being operated upon.

The clinician can use bone preparation guide body 30 to prepare an end of first metatarsal 210 and an end of medial cuneiform 222. The clinician may prepare the ends of one or both bones before or after moving the first metatarsal in one or more planes (e.g., using bone preparation guide body 30). In either case, the clinician may optionally provisionally fixate the moved position (e.g., by inserting a k-wire or other fixation element) into first metatarsal 210 and an adjacent bone (e.g., second metatarsal 212, medial cuneiform 222). The clinician can remove instrument 10 from the foot, e.g., before or after optionally provisionally fixating. In either case, the clinician may permanently fixate the prepare bone ends, causing the prepared bone ends to fuse together. Example fixation devices that may be used to permanently fixate the joint for fusion include, but are not limited to, plates, staples, screws, pins, and combinations thereof. The one or more fixation devices can be installed across the tarsometatarsal joint from the metatarsal to opposed cuneiform to hold the position of the bones relative to each other for fusion.

In one example technique, after customary surgical preparation and access, a bone preparation instrument can be inserted into the joint (e.g., first tarsal-metatarsal joint) to release soft tissues and/or excise the plantar flare from the base of the first metatarsal 210. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

An incision can be made and, if a bone positioning instrument is going to be used, one end (e.g., a tip) of a bone positioning guide inserted on the lateral side of a metatarsal other than the first metatarsal 210, such as the second metatarsal 212. The tip can be positioned proximally at a base of the second metatarsal 212 and a third metatarsal 294 interface.

Before or after attaching the optional bone positioning guide, the clinician can insert instrument 10 into the joint. The clinician can position spacer body 12 into the joint space between first metatarsal 210 and medial cuneiform 222 while simultaneously positioning fulcrum body 14 in the joint space between first metatarsal 210 and second metatarsal 212.

In applications utilizing a bone positioning guide, one or more movable features of the bone positioning guide can be moved to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving a bone engagement member of bone positioning guide with respect to a tip of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Other instrumented and/or non-instrumented approaches can be used to adjust a position of first metatarsal 210 relative to medial cuneiform 222. Thus, other applications utilizing instrument 10 may be performed without utilizing bone positioning guide and/or using a bone positioning guide having a different design than the specific example illustrated herein.

In some applications, the end of the first metatarsal 210 facing the medial cuneiform 222 can be prepared with a tissue removing instrument guided by a guide surface of bone preparation guide body 30 (e.g., inserted through a slot defined by a first guide surface and a first facing surface). In some embodiments, the first metatarsal 210 end preparation is done after at least partially aligning the bones, e.g., by actuating bone positioning guide or otherwise moving the first metatarsal but after preparing the end of first metatarsal 210. In other embodiments, the first metatarsal 210 end preparation is done before the alignment of the bones.

In addition to preparing the end of first metatarsal 210, the end of the medial cuneiform 222 facing the first metatarsal 210 can be prepared with the tissue removing instrument guided by a guide surface of bone preparation guide body 30 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts, or the cuts can be angled relative to each other. In some examples, a saw blade can be inserted through a first slot to cut a portion of the medial cuneiform and the saw blade can be inserted through a second slot to cut a portion of the first metatarsal.

Various examples have been described. These and other examples are within the scope of the following claims.

The invention claimed is:

1. A bone cutting and joint realignment instrument, the instrument comprising:
   a spacer body configured to be inserted into a joint space between a metatarsal and an opposed cuneiform of a foot;
   a bone preparation guide body affixed to the spacer body with the spacer body extending downwardly from the bone preparation guide body, the bone preparation guide body defining at least one guide surface configured to be positioned over at least one of the metatarsal and the opposed cuneiform; and
   a fulcrum body rotatably coupled to the spacer body within a bounded range of rotation of less than 90 degrees, the fulcrum body being configured to be inserted in an intermetatarsal space between the metatarsal and an adjacent metatarsal.

2. The instrument of claim 1, wherein one of the spacer body and the fulcrum body defines a projecting tongue and an other of the spacer body and fulcrum body defines a groove, and the projecting tongue is inserted into the groove to rotatably couple the fulcrum body to the spacer body.

3. The instrument of claim 2, wherein the groove defines an opening cross-sectional size larger than a cross-sectional size of the projecting tongue to allow the projecting tongue to rotate relative to the groove.

4. The instrument of claim 3, wherein the projecting tongue is interlocked in the groove by a locking projection and complementary locking receiving cavity.

5. The instrument of claim 4, wherein:
   the locking projection extends outwardly from a face of the projecting tongue; and
   the complementary locking receiving cavity extends through a wall surface of the other of the spacer body and the fulcrum body defining the groove.

6. The instrument of claim 5, wherein the wall surface of the other of the spacer body and the fulcrum body defining the groove comprises a beam between the complementary locking receiving cavity and an opening of the groove, the beam being configured to bend to facilitate insertion of the locking projection into the groove.

7. The instrument of claim 2, wherein the spacer body defines the projecting tongue and the fulcrum body defines the groove.

8. The instrument of claim 1, wherein the spacer body and the fulcrum body define an angular intersection therebetween, the angular intersection being within a range from 80 degrees to 125 degrees.

9. The instrument of claim 1, wherein the spacer body and the fulcrum body define an angular intersection therebetween, and the fulcrum body is rotatably coupled to the spacer body to allow the angular intersection to adjust from a minimum of approximately 90 degrees to a greater angle.

10. The instrument of claim 9, wherein the bounded range of rotation is approximately 25 degrees or less, and the angular intersection is within a range from 90 degrees to 115 degrees.

11. The instrument of claim 1, wherein the fulcrum body is freely rotatable relative to the spacer body in the bounded range without being lockable at a particular degree of rotation.

12. The instrument of claim 1, further comprising a handle connected to the bone preparation guide body.

13. The instrument of claim 12, wherein the bone preparation guide body has a length extending from a first end to a second end, the spacer body is affixed to the bone preparation guide body at the first end, and the handle is connected to the first end of the bone preparation guide body.

14. The instrument of claim 1, wherein the bone preparation guide body is immovably affixed to the spacer body.

15. The instrument of claim 1, wherein the bone preparation guide body is affixed to the spacer body via a movable connection.

16. The instrument of claim 15, wherein the bone preparation guide body is configured to move perpendicularly relative to the spacer body via the movable connection.

17. The instrument of claim 15, further comprising an actuator operable to adjust a position of the bone preparation guide body relative to the spacer body.

18. The instrument of claim 1, wherein the spacer body defines a first portion configured to extend into the joint space between the metatarsal and the opposed cuneiform and a second portion configured to extend above the joint space, the second portion being offset from the at least one guide surface defined by the bone preparation guide body.

19. The instrument of claim 1, wherein the at least one guide surface defined by the bone preparation guide body has a thickness extending from a top end to a bottom end, the spacer body has a length extending from a top end to a bottom end, and the top end of the spacer body is approximately coplanar with or located vertically below the bottom end of the at least one guide surface.

20. The instrument of claim 1, wherein the bone preparation guide body comprises at least a first guide surface configured to be positioned over the metatarsal and a second guide surface configured to be positioned over the opposed cuneiform, the first and second guide surfaces being separated from each other by a distance configured to span a tarsometatarsal joint.

21. The instrument of claim 20, wherein the first guide surface and the second guide surface each have a thickness less than 2 mm.

22. The instrument of claim 20, wherein the bone preparation guide body further comprises:
a first facing guide surface spaced apart from the first guide surface to define a first cutting slot therebetween, and
a second facing surface spaced apparent from the second guide surface to define a second cutting slot therebetween.

23. The instrument of claim 22, wherein the first facing guide surface and the second facing guide surface each have a thickness less than 2 mm.

24. A bone cutting and joint realignment instrument, the instrument comprising:
a bone preparation guide body defining at least one guide surface configured to be positioned over at least one of a metatarsal and an opposed cuneiform of a foot;
a spacer body extending downwardly from the bone preparation guide body, the spacer body being configured to be inserted into a joint space between the metatarsal and the opposed cuneiform; and
a fulcrum body rotatably coupled to the spacer body within a bounded range of rotation of less than 90 degrees, the fulcrum body being configured to be inserted in an intermetatarsal space between the metatarsal and an adjacent metatarsal.

25. The instrument of claim 24, wherein the at least one guide surface defined by the bone preparation guide body has a thickness extending from a top end to a bottom end, the spacer body has a length extending from a top end to a bottom end, and the top end of the spacer body is approximately coplanar with or located vertically below the bottom end of the at least one guide surface.

26. The instrument of claim 24, wherein the bone preparation guide body comprises at least a first guide surface configured to be positioned over the metatarsal and a second guide surface configured to be positioned over the opposed cuneiform, the first and second guide surfaces being separated from each other by a distance configured to span a tarsometatarsal joint.

27. The instrument of claim 26, wherein the bone preparation guide body further comprises:
a first facing guide surface spaced apart from the first guide surface to define a first cutting slot therebetween, and
a second facing surface spaced apparent from the second guide surface to define a second cutting slot therebetween.

28. The instrument of claim 27, wherein the first facing guide surface and the second facing guide surface each have a thickness less than 1.5 mm.

29. A method comprising;
inserting a bone cutting and joint realignment instrument into joint spaces of the foot, the bone cutting and joint realignment instrument comprising a spacer body, a bone preparation guide body affixed to the spacer body, and a fulcrum body rotatably coupled to the spacer body within a bounded range of rotation, wherein inserting the bone cutting and joint realignment instrument into joint spaces of the foot comprises inserting the spacer body between a metatarsal and an opposed cuneiform of the foot, concurrently inserting the fulcrum body between the metatarsal and an adjacent metatarsal, and concurrently positioning at least one guide surface defined by the bone preparation guide body over one or both of the metatarsal and opposed cuneiform;

preparing an end of the metatarsal by guiding a bone preparation instrument along the at least one guide surface defined by the bone preparation guide body;

preparing an end of the opposed cuneiform by guiding the bone preparation instrument along the at least one guide surface defined by the bone preparation guide body;

moving the metatarsal relative to the adjacent metatarsal; and applying at least one fixation device across a tarsometatarsal joint between a prepared end of the metatarsal and a prepared end of the opposed cuneiform.

30. The method of claim 29, wherein inserting the fulcrum body between the metatarsal and the adjacent metatarsal comprises adjusting a rotational position of the fulcrum body relative to the spacer body within the bounded range of rotation.

31. The method of claim 30, wherein the spacer body and the fulcrum body define an angular intersection therebetween, and adjusting the rotational position of the fulcrum body relative to the spacer body within the bounded range of rotation comprises increasing the angular intersection from 90 degrees or less to more than 90 degrees.

32. The method of claim 29, wherein the spacer body and the fulcrum body define an angular intersection therebetween, and the angular intersection is within a range from 80 degrees to 125 degrees.

33. The method of claim 29, wherein the bounded range of rotation is less than 60 degrees.

34. The method of claim 29, wherein the bone preparation guide body is affixed to the spacer body via a movable connection, and further comprising, after inserting the bone cutting and joint realignment instrument into joint spaces of the foot, moving the bone preparation guide body relative to the spacer body via the movable connection in a medial-to-lateral direction.

35. The method of claim 29, wherein:
the at least one guide surface defined by the bone preparation guide body comprises a first guide surface configured to be positioned over the metatarsal and a second guide surface configured to be positioned over the opposed cuneiform, and
positioning the at least one guide surface defined by the bone preparation guide body over one or both of the metatarsal and opposed cuneiform comprises positioning the first guide surface over the metatarsal and the second guide surface over the opposed cuneiform.

36. The method of claim 29, wherein:
the metatarsal is a first metatarsal,
the opposed cuneiform is a medial cuneiform, and
the adjacent metatarsal is a second metatarsal.

37. The method of claim 29, wherein:
preparing the end of the metatarsal and preparing the end of the opposing cuneiform comprises preparing one or both of the end of the metatarsal and the end of the opposed cuneiform after moving the metatarsal relative to the adjacent metatarsal;
moving the metatarsal relative to the adjacent metatarsal comprises moving the metatarsal in at least a transverse plane, thereby pivoting the metatarsal about the fulcrum body and reducing an intermetatarsal angle between the metatarsal and the adjacent metatarsal; and
the fixation device comprise at least one of a plate, a staple, and a screw.

* * * * *